(12) United States Patent
Heanue et al.

(10) Patent No.: US 10,274,413 B2
(45) Date of Patent: *Apr. 30, 2019

(54) BEAM SHAPING OPTICS OF FLOW CYTOMETER SYSTEMS AND METHODS RELATED THERETO

(71) Applicant: Abbott Laboratories, Abbott Park, IL (US)

(72) Inventors: John F. Heanue, Manchester, MA (US); Stuart L. Friedman, Palo Alto, CA (US)

(73) Assignee: Abbott Laboratories, Abbott Park, IL (US)

( * ) Notice: Subject to any disclaimer, the term of this patent is extended or adjusted under 35 U.S.C. 154(b) by 250 days.

This patent is subject to a terminal disclaimer.

(21) Appl. No.: 15/348,817

(22) Filed: Nov. 10, 2016

(65) Prior Publication Data

US 2017/0115202 A1    Apr. 27, 2017

Related U.S. Application Data

(63) Continuation of application No. 14/212,185, filed on Mar. 14, 2014, now Pat. No. 9,523,857.

(Continued)

(51) Int. Cl.
*G01N 15/14* (2006.01)
*G02B 27/09* (2006.01)
*G01N 15/10* (2006.01)

(52) U.S. Cl.
CPC ..... *G01N 15/1434* (2013.01); *G01N 15/1459* (2013.01); *G02B 27/0927* (2013.01);
(Continued)

(58) Field of Classification Search
CPC ............... G01N 15/14; G01N 15/1404; G01N 2015/1413; G01N 15/1434;
(Continued)

(56) References Cited

U.S. PATENT DOCUMENTS 4,327,972 A      5/1982   Brunsting
6,201,229 B1 *   3/2001   Tawa ................... B23K 26/032
                                                    250/201.5
(Continued)

FOREIGN PATENT DOCUMENTS

JP    04-184241 H    7/1992
JP    11-258544 H    9/1999
(Continued)

*Primary Examiner* — John R Lee
(74) *Attorney, Agent, or Firm* — Edward J. Baba; Payal B. Sud; Bozicevic, Field & Francis LLP (57) ABSTRACT

In some aspects, a flow cytometer system is provided that includes beam shaping optics positioned to manipulate a light beam and produce a resulting light beam that irradiates the core stream at the interrogation zone of the flow cell. The beam shaping optics include an acylindrical lens positioned to receive and focus light in a direction of a first axis orthogonal to a direction of light travel, and a cylindrical lens positioned to receive the light output from the acylindrical lens and to focus the light output from the acylindrical lens in a direction of a second axis orthogonal to the first axis and to the direction of light travel. The resulting light beam output has a flat-top shaped intensity profile along the first axis, and a Gaussian-shaped intensity profile along the second axis. Related methods of shaping a light beam at an interrogation zone of a flow cell are also provided.

20 Claims, 5 Drawing Sheets

Related U.S. Application Data

(60) Provisional application No. 61/785,922, filed on Mar. 14, 2013.

(52) U.S. Cl.
CPC . *G02B 27/0966* (2013.01); *G01N 2015/1006* (2013.01); *G01N 2201/068* (2013.01)

(58) Field of Classification Search
CPC ........... G01N 15/1436; G01N 15/1456; G01N 15/1459; G01N 2015/1006; G01N 2201/068; G02B 27/0927; G02B 27/0966
See application file for complete search history.

(56) References Cited

U.S. PATENT DOCUMENTS

| | | | |
|---|---|---|---|
| 9,523,857 B2 * | 12/2016 | Heanue | G02B 27/0927 |
| 2005/0170572 A1 | 8/2005 | Hongo et al. | |
| 2008/0165425 A1 | 7/2008 | Cayer | |
| 2008/0186490 A1 | 8/2008 | Chu | |
| 2009/0174881 A1 | 7/2009 | Rich | |
| 2010/0220315 A1 | 9/2010 | Morrell et al. | |
| 2012/0019824 A1 * | 1/2012 | Dowaki | G01N 15/1434 356/337 |
| 2014/0264097 A1 * | 9/2014 | Heanue | G02B 27/0927 250/576 |
| 2017/0115202 A1 * | 4/2017 | Heanue | G02B 27/0927 |

FOREIGN PATENT DOCUMENTS

| | | |
|---|---|---|
| JP | 2002-90284 A | 3/2002 |
| WO | 01/098760 | 12/2001 |

* cited by examiner

BEAM SHAPING OPTICS OF FLOW CYTOMETER SYSTEMS AND METHODS RELATED THERETO

CROSS-REFERENCE

This application is a continuation of U.S. patent application Ser. No. 14/212,185 filed Mar. 14, 2014, issued as U.S. Pat. No. 9,523,857, which claims the benefit of U.S. Provisional Patent Application No. 61/785,922 filed Mar. 14, 2013, which applications are incorporated herein by reference in their entirety.

SUMMARY

In some aspects of the present disclosure, a flow cytometer system is provided. The flow cytometer system includes a flow cell for streaming a hydro-dynamically focused core stream past an interrogation zone, and beam shaping optics positioned to receive and manipulate a first light beam, and to produce a resulting light beam that irradiates the core stream at the interrogation zone of the flow cell. The beam shaping optics include an acylindrical lens positioned to receive and focus light in a direction of a first axis orthogonal to a direction of light travel, and a cylindrical lens positioned to receive the light output from the acylindrical lens and to focus the light output from the acylindrical lens in a direction of a second axis orthogonal to the first axis and to the direction of light travel. The resulting light beam output from the beam shaping optics has a flat-top shaped intensity profile along the first axis, and a Gaussian-shaped intensity profile along the second axis.

In some aspects of the present disclosure, a method of shaping a light beam at an interrogation zone of a flow cell is provided. The method includes streaming a hydro-dynamically focused core stream past an interrogation zone in a flow cell; and receiving and manipulating a first light beam with beam shaping optics to produce a resulting light beam that irradiates the core stream at the interrogation zone of the flow cell. The receiving and manipulating of the first light beam with the beam shaping optics includes receiving and focusing light with an acylindrical lens in a direction of a first axis orthogonal to a direction of light travel; and receiving and focusing the light output from the acylindrical lens with a cylindrical lens. The cylindrical lens focuses the light output from the acylindrical lens in a direction of a second axis orthogonal to the first axis and to the direction of light travel. The resulting light beam output from the beam shaping optics has a flat-top shaped intensity profile along the first axis, and a Gaussian-shaped intensity profile along the second axis.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the systems and methods presented. In the drawings, like reference numbers indicate identical or functionally similar elements.

DETAILED DESCRIPTION

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

The present disclosure relates generally to beam shaping optics that provide a uniform intensity distribution light beam. The beam shaping optics may relate to flow cytometers, such as used in conjunction with hematology instruments or analysis. The beam shaping optics may also be relevant to a variety of technologies, such as, but not limited to, scanning microscopy, holography, optical bar code scanners, etc.

In some aspects of the present disclosure, beam shaping optics are provided that provide a light beam with an intensity profile that is Gaussian shaped along one axis that is orthogonal to the direction of light travel, and flat-top shaped along another axis that is orthogonal to both the axis of the Gaussian shaped profile and to the direction of light travel. The beam shaping optics include an acylindrical lens positioned to receive and focus light in a direction of a first axis orthogonal to a direction of light travel, and a cylindrical lens positioned to receive the light output from the acylindrical lens and to focus the light output from the acylindrical lens in a direction of a second axis orthogonal to the first axis and to the direction of light travel.

The acylindrical lens has a curved surface that has a curvature that does not have a constant radius. The radius of the curvature of the acylindrical lens varies. For example, in one embodiment, the radius of curvature is non-constant with the shortest radius at the axis of symmetry, and the radius increasing away from the axis of symmetry. In one embodiment, the radius of curvature follows a polynomial equation that is an even order polynomial and a conic contribution, such as, but not limited to, an even order twelfth-order polynomial or less. For instance, the polynomial equation may be represented by the following equation:

$$R = ax^2 + bx^4 + cx^6 + dx^8 + ex^{10} + fx^{12}$$

wherein R is the radius of curvature, and a, b, c, d, e, and f are constants of the polynomial equation. In one embodiment, the acylindrical lens is a plano-convex acylindrical lens, which has a planar side on one side and a convex curvature on an opposite side.

The cylindrical lens has a curved surface that has a curvature that has a constant radius which does not vary. In one embodiment, the cylindrical lens is a plano-convex cylindrical lens, which has a planar side on one side and a convex curvature on an opposite side. The cylindrical lens is positioned with its axis of symmetry orthogonal to the axis of symmetry of the acylindrical lens. In this way, the cylindrical lens receives the light beam from the acylindrical lens and focuses it along an axis orthogonal to focusing axis of the acylindrical lens and the direction of the light.

While the embodiments and descriptions may refer to "horizontal" and "vertical" axes or intensity profiles, it should be understood that the terms are used to provide relative axis orientations and to facilitate understanding. It should be understood that the underlying concepts and principles of the present disclosure are also applicable to other embodiments, wherein the "vertical" beam profile is a flat-top profile and the "horizontal" beam profile is a Gaussian curve—e.g., with the core stream flowing horizontally.

In some aspects of the present disclosure, a flow cytometer system is provided. The flow cytometer system includes a flow cell for streaming a hydro-dynamically focused core stream past an interrogation zone, and beam shaping optics positioned to receive and manipulate a first light beam, and to produce a resulting light beam that irradiates the core stream at the interrogation zone of the flow cell. The beam shaping optics include an acylindrical lens positioned to receive and focus light in a direction of a first axis orthogonal to a direction of light travel, and a cylindrical lens positioned to receive the light output from the acylindrical lens and to focus the light output from the acylindrical lens in a direction of a second axis orthogonal to the first axis and to the direction of light travel. The resulting light beam output from the beam shaping optics has a flat-top shaped intensity profile along the first axis, and a Gaussian-shaped intensity profile along the second axis.

The flat-top shaped intensity profile includes a step-like shape that has a generally flatter top portion which decreases to lower intensity values to each side of the flatter top portion. The flatter top portion corresponds to a larger magnitude of intensity than the smaller side values. The flatter top portion of the flat-top profile is flatter (or maintains a more constant level of magnitude) than a corresponding top portion of a Gaussian shaped profile. The degree of flatness may be defined by the coefficient of variation of the top portion of the intensity profile. The coefficient of variation (CV) may be represented as the standard deviation divided by the mean. The coefficient of variation may vary in different embodiments. In one embodiment, the top portion of the flat-top profile has a coefficient of variation of less than 5%. In another embodiment, the top portion of the flat-top profile has a coefficient of variation of less than 3%. In yet another embodiment, the top portion of the flat-top profile has a coefficient of variation of less than 1%. Having a uniform intensity distribution profiled light beam spot of small dimensions, as present with the flat-top intensity profile, provides many benefits for flow cytometry by ensuring precise differential of various cellular components in an assay. For example, the mean and standard deviation is improved without wasting laser power. Moreover, greater scatter signals may be obtained for the same laser power as used in conventional methods. Furthermore, the flat-top intensity profile maintains precise polarization, which may prove beneficial for measurements of depolarization of scatter light from cells. Furthermore, the implementation of an acylindrical lens as described herein enables better control of producing a flat-top profile. The acylindrical lens enables a wide flat top portion for the entire profile. Moreover, the acylindrical lens enables the system to be more compact in that the positioning between the two lenses (e.g., acylindrical and cylindrical) may be smaller. For example, in one embodiment, the distance between the two lenses may be within the range of 15 mm to 30 mm. In one embodiment, the distance between the two lenses may be within 20-25 mm, such as approximately 23 mm. The distances are exemplary and other distances may be implemented in other embodiments. The spacing between the lenses may depend on various factors, such as on how far the focus point need to be, how small the spot size need to be, etc. Furthermore, in one embodiment, the usable flat-top range may be approximately 0.5 mm. It should be appreciated that this is exemplary and should not be construed as limiting, and that other sizes of usable flat-top range may be implemented in other embodiments.

In one embodiment, the flow cytometer system may include the light source that provides light to the beam shaping optics. For example, the light source may include a laser coupled to an optical fiber to generate a laser beam directed to the beam shaping optics positioned between the light source and flow cell. The beam shaping optics may include, for example, a collimating lens to collimate the light before being manipulated by the acylindrical and cylindrical lens. In some instances, the collimating lens is an aspheric collimating lens.

The flow cell is positioned such that the light from the beam shaping optics is directed to an interrogation zone in the flow cell. The flow cell includes a core stream which is flows past the interrogation zone of the flow cell, and is irradiated by the resulting focused light as it passes through the interrogation zone. The resulting light beam output from the beam shaping optics has a flat-top shaped intensity profile along a first axis which is orthogonal to the direction of light travel, and a Gaussian-shaped intensity profile along a second axis, which is orthogonal to both the first axis and to the direction of light travel.

The core stream 122 may include, for example, samples which are hydro-dynamically focused in a fluid sheath (e.g., injected into the center of the fluid sheath) and directed past the interrogation zone in the flow cell. In one embodiment, the samples are hydro-dynamically focused in the fluid sheath to produce a core stream having a sample stream that is generally only a single sample wide. The sheath fluid may be, for example, water, saltwater, or other diluting agent, alone or with any variety of chemicals for various purposes. It should be appreciated that coincident cells (e.g., more than one sample wide) may occur randomly from time to time. Example samples may include, but are not limited to particles or cells, such as white blood cells, red blood cells, platelets, beads, poly dispersed oil droplets, hematology controls, etc. The size of the samples varies depending on the particular size of the samples, for instance.

When the core stream flows in the same direction in which the cylindrical lens focuses the light, the core stream flows in the same direction as the Gaussian shaped intensity profile, and all samples flowing through the interrogation zone of the flow cell encounter the same amount of light along due to the Gaussian shaped profile. For example, the core stream may flow vertically and be exposed to a vertical Gaussian shaped intensity profile as it passes vertically through the interrogation zone.

However, when the size of the samples is smaller than the size of the core stream, the radial position of the samples within the core stream may vary. For example, if the core stream is flowing vertically, the core stream has a horizontal width in which the samples may vary horizontally. The flat-top profile may be used to provide a constant level of intensity for samples at different positions horizontally. For instance, the flattened top portion of the flat-top profile may be equal to or wider than the core stream to provide the same amount of light horizontally across the core stream. In one embodiment, the flattened top portion of the flat-top profile is wider than the core stream to provide the same amount of light horizontally across the core stream. In some instances, tolerances for movement of the core stream may also be accounted for. In this way, when a detection system detects various data (e.g., axial light loss, scattered light, etc. from the flow cell), a higher level of certainty is achieved that the data is accurate because there is less variation in the amount of light interrogating the sample. In certain situations, the horizontal flat-top beam profile also provides the benefit of enabling the implementing of a wider core stream for instance.

It should be appreciated that the size of the intensity profiles (e.g., width of the flattened top portion of the flat-top profile), the size of the core stream, the size of the samples, the pressure and speed of the sheath fluid, the size of the interrogation zone, etc., may each vary in different embodiments depending the specific parameters desired. Furthermore, the distance and positioning of the beam shaping optics with respect to each other and the flow cell may vary, in order to account for specific parameters chosen above. For example, the acylindrical lens and cylindrical lens should be positioned at corresponding distances from each other and the flow cell to provide for a horizontal flat-top intensity profile that will have the flattened top portion equal to or greater than the horizontal width of the core stream in which the samples may vary.

Example Embodiments Shown in the Figures

Figure 1:
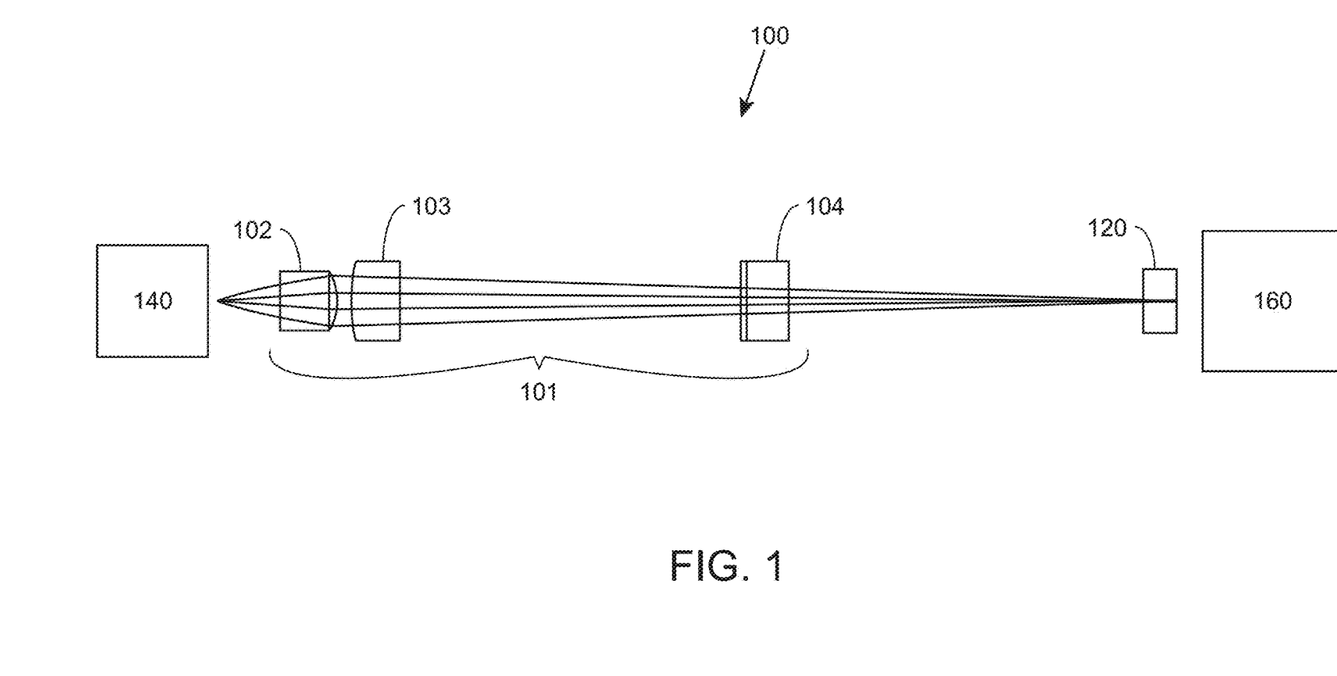
FIG. 1 illustrates a flow cytometer system, according to one embodiment.

FIG. 1 illustrates a top view of a flow cytometer system, according to one embodiment. Flow cytometer system 100 is shown including beam shaping optics 101, flow cell 120, light source 140, and detection system 160. Light source 140 may include, for example, a laser coupled to an optical fiber to generate a laser beam directed to the beam shaping optics 101 positioned between the light source 140 and flow cell 120. The laser beam is manipulated by the beam shaping optics 101 to provide a focused beam directed to an interrogation zone 121 of the flow cell 120. A core stream within the flow cell 120 is irradiated by the focused beam as it flows past the interrogation zone of the flow cell 120. The core stream 122 and interrogation zone 121 are shown more clearly in FIGS. 2 and 7. At the interrogation zone 121, the beam shaping optics 101 produce a focused beam having specifically shaped intensity profiles along axes which are orthogonal to the direction of travel of the laser beam.

Beam shaping optics 101 is shown including a collimating lens 102, acylindrical lens 103, and cylindrical lens 104. The collimating lens 102 is positioned to receive a light beam and produce collimated light directed to the acylindrical lens 103. The acylindrical lens 103 is positioned to receive the collimated light and focus the light along a single axis orthogonal to the direction of the light. For example, a light exiting the acylindrical lens may converge in the vertical plane. The cylindrical lens 104 is positioned with its axis of symmetry orthogonal to the axis of symmetry of the acylindrical lens. In this way, the cylindrical lens 104 receives the light beam from the acylindrical lens 103 and focuses it along an axis orthogonal to focusing axis of the acylindrical lens 103 and the direction of the light.

Flow cell 120 is positioned such that the light from the beam shaping optics 101 is directed to an interrogation zone in the flow cell 120. Flow cell 120 includes a core stream 122 which is directed past the interrogation zone 121 of the flow cell 120. In this way, the core stream 122 flowing through the flow cell 120 is irradiated by the focused light as it passes through the interrogation zone 121. The core stream 122 may include, for example, samples which are hydro-dynamically focused in a fluid sheath (e.g., injected into the center of the fluid sheath) and directed past the interrogation zone 121 in the flow cell 102. In one embodiment, the samples are hydro-dynamically focused in the fluid sheath to produce a core stream having a sample stream that is generally only a single sample wide.

The width of the core stream may vary in different embodiments. In one embodiment, for example, the width of the core stream includes, but is not limited to, a width within 10-30 microns, such as 15-25 microns. The pressure and speed of the core stream may in different embodiments. For example, the pressure of the core stream may include, but is not limited to, a pressure of 8-20 pounds per square inch, such as 10-15 pounds per square inch. Moreover, the speed of the core stream may include, but is not limited to, a speed of approximately 5-15 meters per second, such as 8-12 meters per second.

Detection system 160 is positioned next to the flow cell to detect light emitted from the flow cell. For example, detection system 160 may include one or more detectors to detect axial light loss and/or one or more detectors to measure the amount of scattered light resulting from when the core stream is irradiated by the focused light beam at the interrogation zone. For instance, the detection system 160 may include one or more detectors to detect intermediate angle scatter (IAS) and/or forward scatter.

Figure 2:
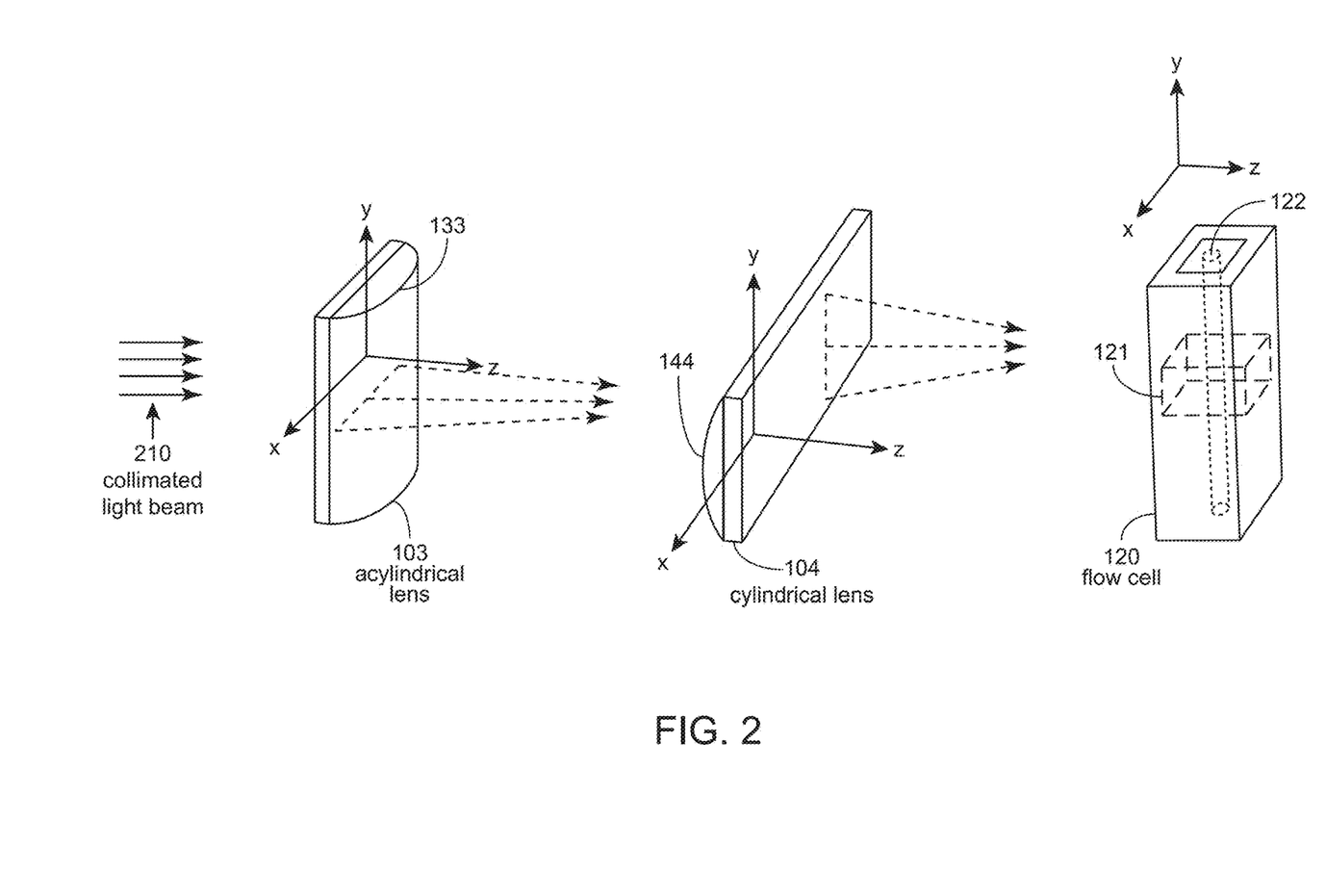
FIG. 2 illustrates a close up perspective view of an exemplary beam shaping optics and flow cell, according to one embodiment.

The detection system 160 may also include lenses and detectors for detecting fluorescent light, polarized side scatter, and/or depolarized side scatter. Furthermore, one or more detectors may be positioned in various positions around the flow cell—e.g., at 90 degrees from the flow cell. The detection system 160 may also include other components such as lenses, reflectors or mirrors, etc., which are not shown. For example, detection system 160 may include components such as lenses, reflectors or mirrors, etc. It FIG. 2 illustrates a close up perspective view of an exemplary beam shaping optics and flow cell of the flow cytometer system 100 shown in FIG. 1, according to one embodiment. The x, y, and z axes are illustrated and shown for reference purposes.

Acylindrical lens 103 is positioned with its axis of symmetry in the vertical direction along the y-axis. The acylindrical lens shown is plano-convex with a planar side and convex side. The radius of curvature of the convex side 133 varies and is not constant. Collimated light 210, such as produced by collimating lens 102 shown in FIG. 1, travels in the z-direction towards the planar side of the acylindrical lens 103. In some embodiments, the output from the optical fiber coupled to the laser is first expanded. For example, in one embodiment, the output from the optical fiber coupled to the laser may have approximately a 5 micron circular spot diameter at the fiber tip and may be expanded to approximately 1000 micron circular spot diameter.

Figure 3:
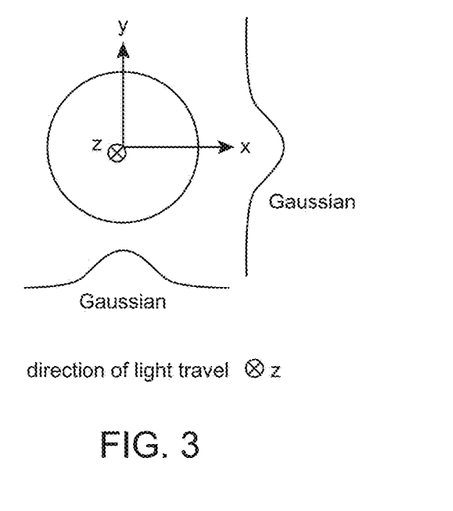
FIG. 3 illustrates an exemplary intensity profile for the collimated light in FIG. 2.

FIG. 3 illustrates an intensity profile 211 for the collimated light 210. The collimated light 210, as shown, travels into the paper along the z-axis. In the x-y plane, the intensity profile 211 for the collimated light 210 is Gaussian shaped horizontally along the x-axis and vertically along the y-axis.

Figure 4:
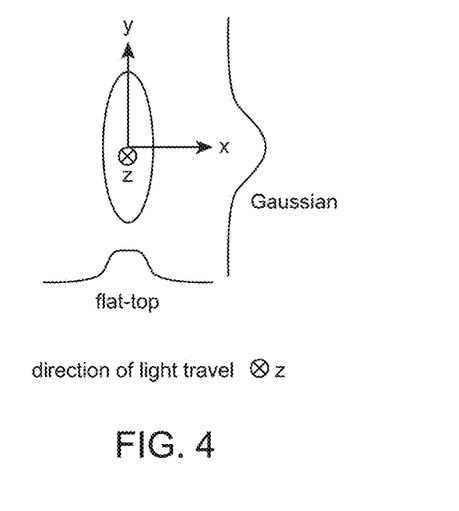
FIG. 4 illustrates an exemplary intensity profile generated for light passing through the acylindrical lens in FIG. 2.

Returning to FIG. 2, the planar side of acylindrical lens 103 receives the collimated light 210 and focuses the light along the x-axis as it exits the convex side of acylindrical lens 103. For example, the long focal length of the acylindrical lens positioned at a distance converges the light in the horizontal plane over a distance to the interrogation zone of the flow cell. The intensity profile gradually varies as the light travels further away from the acylindrical lens 103. As shown in FIG. 4, the intensity profile 213 generated by the acylindrical lens 103 becomes smaller in width and generally flat-top shaped horizontally along the x-axis. The intensity profile 213 remains Gaussian shaped vertically along the y-axis.

The cylindrical lens 104 is positioned in the path of the focused light exiting the acylindrical lens 103. The cylindrical lens 104 is positioned with its axis of symmetry along the x-axis, which is perpendicular to the axis of symmetry of the acylindrical lens 103 along the y-axis. Both the x and y axes are orthogonal to the direction of travel of the light. The cylindrical lens 104 shown is plano-convex with its convex side receiving the focused light from the acylindrical lens 103. The radius of curvature of the convex side 144 of the cylindrical lens 104 is constant.

Figure 5:
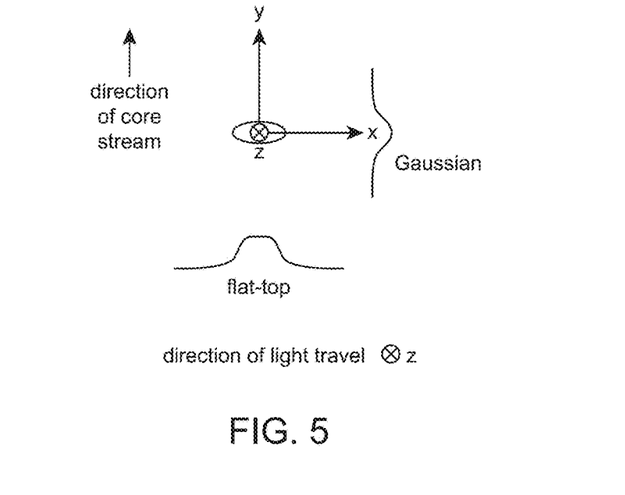
FIG. 5 illustrates an exemplary intensity profile generated for light passing through both the acylindrical lens and cylindrical lens in FIG. 2.

The cylindrical lens 104 focuses the light along the y-axis as it exits the planar side of cylindrical lens 104. The shorter focal length of the cylindrical lens in the orthogonal orientation focuses the beam in in the vertical plane. The intensity profile gradually varies as the light travels further away from the cylindrical lens 104. As shown in FIG. 5, the intensity profile 215 generated by the cylindrical lens 103 becomes smaller in width and remains Gaussian shaped vertically along the y-axis. The intensity profile 215 remains flat-top shaped horizontally along the x-axis. The focusing of the light along the y-axis also contributes to further flattening of the top of the flat-top shaped profile. The net result of the mutually independent focusing at the core stream has a flat-top profile horizontally and a Gaussian profile vertically over a small distance encompassing the core stream.

Figure 6:
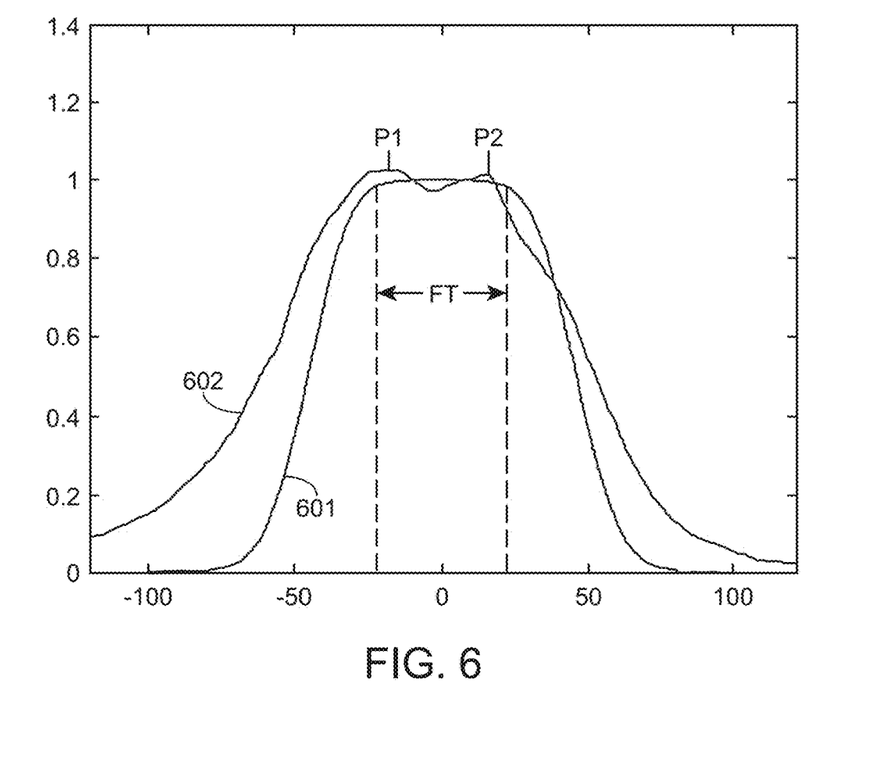
FIG. 6 illustrates a flat-top shaped intensity profile generated by the beam shaping optics 101, according to one embodiment, according to one embodiment.

FIG. 6 illustrates a flat-top shaped intensity profile generated by the beam shaping optics 101, according to one embodiment. The vertical axis of the graph represents the magnitude of intensity of the light (e.g., $W/cm^2$), while the horizontal axis of the graph represents the horizontal distance (e.g., microns) along the x-axis.

Intensity profile 601 is a flat-top shaped horizontal intensity profile generated by the beam shaping optics 101 at the interrogation zone 121 of the flow cell 120 in FIG. 2. Also shown for comparison purposes is the ideal intensity profile 602.

The flat-top shaped intensity profile includes a step-like shape that has a generally flatter top portion which decreases to lower intensity values to each side of the flatter top portion. The flatter top portion corresponds to a larger magnitude of intensity than the smaller side values. The flatter top portion of the flat-top profile is flatter (or maintains a more constant level of magnitude) than, for example, a corresponding top portion of a Gaussian shaped profile. The degree of flatness may be defined by the coefficient of variation of the flattened top portion of the flat-top intensity profile. In one embodiment, the top portion FT of profile 601 has a coefficient of variation of less than 5%. In another embodiment, the top portion has a coefficient of variation of less than 3%. In yet another embodiment, the top portion has a coefficient of variation of less than 1%.

Profile 602 includes a generally flattened top portion. While the top portion is not completely flat, it is referred to as "generally flattened" because the top portion is flattened with respect to the curvature of a corresponding portion of a Gaussian shaped profile.

When the cylindrical lens 104 is implemented and focuses the light vertically along the y-axis, the top portion of the profile is flattened out further, as represented by profile 601. Furthermore, the steepness of the slopes on the sides is increased. In the embodiment shown in FIG. 6, the top portion FT of profile 601 has a coefficient of variation of less than 1% over approximately 40 micron by 40 micron region (e.g., 40 microns across x-axis over 40 microns across z-axis). For example, the 40 micron wide flattened top portion FT is able to provide an approximately constant intensity of light across a core stream that is 40 microns wide or smaller—e.g., 10-25 microns wide.

The width of the flattened top portion FT of a flat-top intensity profile may vary in different embodiments. In one embodiment, for example, the width of the flattened top portion FT of a flat-top intensity profile includes, but is not limited to, a width within 30-80 microns wide, such as 40-65 microns.

Returning to FIG. 2, the flow cell 120 is positioned in the path of the focused light exiting the cylindrical lens 104. The flow cell is positioned so that the focused light is directed to an interrogation zone 121 and irradiates the core stream 122 passing vertically along the y-axis through the interrogation zone 121.

Figure 7:
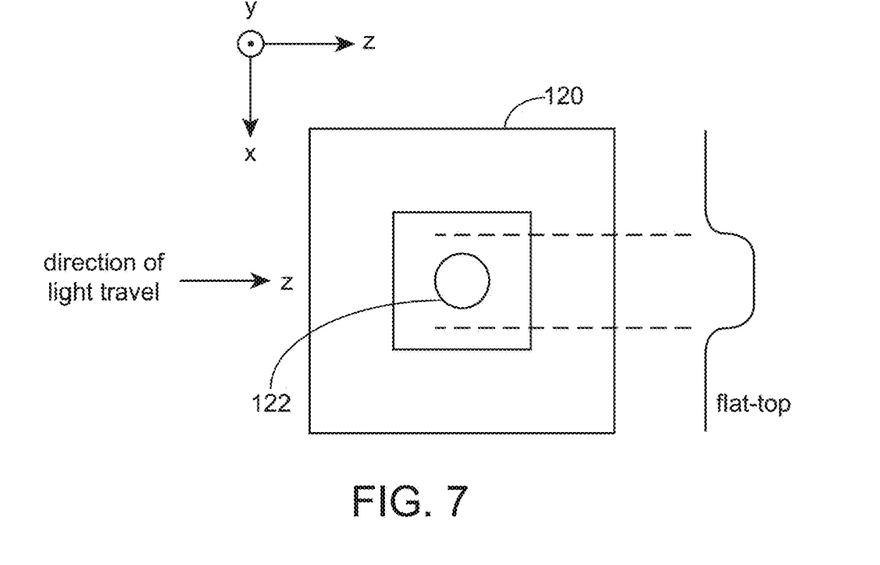
FIG. 7 illustrates a top view of an exemplary flow cell in FIG. 2.

The distance the flow cell is from the beam shaping optics may vary in different embodiments, but should generate an intensity profile at the interrogation zone that is Gaussian shaped vertically along the y-axis and flat-top shaped horizontally along the x-axis. For example, in one embodiment, the flat-top shape in the horizontal position resembles the intensity profile 601 shown in FIG. 6. The width of the top portion of the flat-top shaped intensity profile may vary in different embodiments. Having the horizontal width of the top portion of the flat-top shaped intensity profile equal to or larger than the horizontal width of the core stream 122 in the interrogation zone 121 ensures that each sample in the core stream 122 is exposed to the approximately the same amount of light irrespective of the sample's horizontal position within the core stream. The difference in the amount of light will be limited by the coefficient of variation (e.g., 1% or less) of the flat-top profile implemented. For example, FIG. 7 illustrates a top view of the flow cell 120 in FIG. 2. Flow cell 120 includes a core stream 122 flowing in the y-axis (e.g., out of the paper). The focused light from the beam shaping optics 101 is traveling in the z-direction towards the flow cell 120. At the interrogation zone 121 (shown more clearly in FIG. 2) of the flow cell 120, the focused light has a horizontal intensity profile along the x-axis that is shaped as a flat-top. In one embodiment, the width of the flattened top portion of the horizontal intensity profile is larger than the width of the core stream, as represented in FIG. 7 by the dotted lines. In this way, despite a sample's horizontal position in the core stream, the same amount of light is encountered. For example, in one embodiment, the core stream is between 15-25 microns wide along the x-axis and the flattened top portion of the horizontal intensity profile is between 35 and 70 microns wide. It should be appreciated that these sizes are exemplary and that other sizes may be implemented in other embodiments.

While the vertical intensity profile along the y-axis is Gaussian shaped, each sample travels the entire vertical distance of the interrogation zone and is exposed to the same amount of light from the Gaussian shaped vertical intensity profile.

Figure 8:
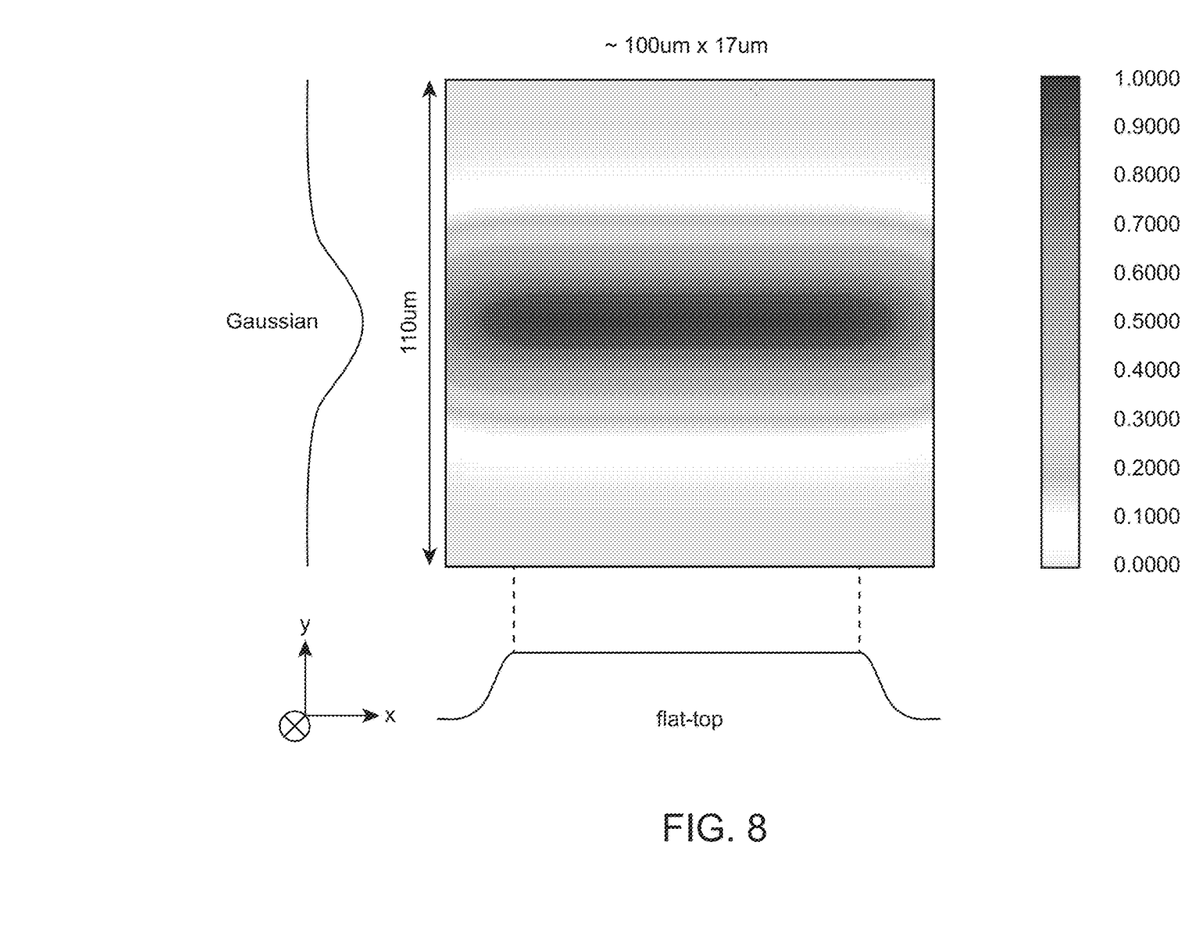
FIG. 8 illustrates an intensity profile for the focused light beam at the interrogation zone of the flow cell in FIG. 2, according to one embodiment.

FIG. 8 illustrates the intensity profile for the focused light beam at the interrogation zone of the flow cell, according to one embodiment. The intensity profile 800 is shown having a Gaussian shape in the vertical direction along the y-axis, and flat-top shaped in the horizontal direction along the x-axis. The flattened top portion FT of the horizontally flat-top shaped profile ensures that samples are exposed to the same amount of light irrespective of their horizontal position along the x-axis.

Additional Example Embodiments

In some aspects of the present disclosure, a flow cytometer system is provided. The flow cytometer system includes a flow cell for streaming a hydro-dynamically focused core stream past an interrogation zone, and beam shaping optics positioned to receive and manipulate a first light beam, and to produce a resulting light beam that irradiates the core stream at the interrogation zone of the flow cell. The beam shaping optics include an acylindrical lens positioned to receive and focus light in a direction of a first axis orthogonal to a direction of light travel, and a cylindrical lens positioned to receive the light output from the acylindrical lens and to focus the light output from the acylindrical lens in a direction of a second axis orthogonal to the first axis and to the direction of light travel. The resulting light beam output from the beam shaping optics has a flat-top shaped intensity profile along the first axis, and a Gaussian-shaped intensity profile along the second axis.

In one embodiment, the core stream flows in a direction of the second axis, and wherein a flattened top portion of the flat-top shaped intensity profile along the first axis is equal to or wider than a width of the core stream along the second axis.

In one embodiment, the flattened top portion of the flat-top shaped intensity profile has a coefficient of variation of less than 5%. In some instances, the flattened top portion of the flat-top shaped intensity profile has a coefficient of variation of less than 3%. In some instances, the flattened top portion of the flat-top shaped intensity profile has a coefficient of variation of less than 1%.

In one embodiment, the acylindrical lens is plano-convex and positioned to receive light on a planar side of the acylindrical lens and to output light on a convex side of the acylindrical lens. The cylindrical lens is plano-convex and positioned to receive light on a convex side of the cylindrical lens and to output light on a planar side of the cylindrical lens. The acylindrical lens has an axis of symmetry orthogonal to an axis of symmetry of the cylindrical lens.

In one embodiment, the beam shaping optics includes a collimating lens, the acylindrical lens positioned between the collimating lens and the cylindrical lens.

In one embodiment, the flow cytometer system includes a light source to provide the first light beam; the light source including a fiber coupled to a laser.

In one embodiment, the flow cytometer system includes a detection system to detect light from the flow cell.

In one embodiment, the core stream includes a sample stream positioned within a sheath fluid, wherein the sample stream is generally a single sample wide.

In some aspects of the present disclosure, a method of shaping a light beam at an interrogation zone of a flow cell is provided. The method includes streaming a hydro-dynamically focused core stream past an interrogation zone in a flow cell; and receiving and manipulating a first light beam with beam shaping optics to produce a resulting light beam that irradiates the core stream at the interrogation zone of the flow cell. The receiving and manipulating of the first light beam with the beam shaping optics includes receiving and focusing light with an acylindrical lens in a direction of a first axis orthogonal to a direction of light travel; and receiving and focusing the light output from the acylindrical lens with a cylindrical lens. The cylindrical lens focuses the light output from the acylindrical lens in a direction of a second axis orthogonal to the first axis and to the direction of light travel. The resulting light beam output from the beam shaping optics has a flat-top shaped intensity profile along the first axis, and a Gaussian-shaped intensity profile along the second axis.

In one embodiment, the core stream flows in a direction of the second axis, and wherein a flattened top portion of the flat-top shaped intensity profile along the first axis is equal to or wider than a width of the core stream along the second axis.

In one embodiment, the flattened top portion of the flat-top shaped intensity profile has a coefficient of variation of less than 5%. In some instances, the flattened top portion of the flat-top shaped intensity profile has a coefficient of variation of less than 3%. In some instances, the flattened top portion of the flat-top shaped intensity profile has a coefficient of variation of less than 1%.

In one embodiment, the acylindrical lens is plano-convex and positioned to receive light on a planar side of the acylindrical lens and to output light on a convex side of the acylindrical lens. The cylindrical lens is plano-convex and positioned to receive light on a convex side of the cylindrical lens and to output light on a planar side of the cylindrical lens. The acylindrical lens has an axis of symmetry orthogonal to an axis of symmetry of the cylindrical lens.

In one embodiment, the beam shaping optics includes a collimating lens, the acylindrical lens positioned between the collimating lens and the cylindrical lens.

In one embodiment, the method includes providing the first light beam with a light source, the light source including a fiber coupled to a laser.

In one embodiment, the method includes detecting light from the flow cell with a detection system. The method may also include processing the detected light from the flow cell to provide various parameters, characteristics, etc., of one or more samples in the core stream. For example, data from the detectors may be used to provide various scatter plots, etc. for the samples to identify or differentiate the samples, count samples, etc. The data may be processed by one or more processors of a computer system, for example, that is communicably coupled to the detection system.

In one embodiment, the core stream includes a sample stream positioned within a sheath fluid, wherein the sample stream is generally a single sample wide.

In one embodiment, the core stream includes a sample stream positioned within a sheath fluid, wherein the sample stream is generally a single sample wide.

It should be appreciated that the previous description for the flow cytometer system may apply equally to the method of shaping a light beam at an interrogation zone of a flow cell. For the sake of clarity and brevity, the common features will not be described in great detail again.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example.

It should be understood that some of the techniques introduced above, such as the detection and processing of the data from the flow cytometry, the control of the light source, etc., can be implemented by programmable circuitry programmed or configured by software and/or firmware, or they can be implemented entirely by special-purpose "hard-wired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The preceding examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

That which is claimed is:

1. A method for interrogating a sample, comprising:
   streaming the sample as a hydro-dynamically focused core stream past an interrogation zone in a flow cell;
   manipulating a first light beam with beam shaping optics to produce a resulting light beam for irradiating the core stream at the interrogation zone of the flow cell, wherein the manipulating of the first light beam comprises:
   focusing the first light beam with an acylindrical lens in a direction of a first axis orthogonal to a direction of light travel;
   focusing light output from the acylindrical lens with a cylindrical lens, wherein the cylindrical lens is positioned within a range of 15 mm to 30 mm from the acylindrical lens, wherein the cylindrical lens focuses the light output from the acylindrical lens in a direction of a second axis orthogonal to the first axis and to the direction of light travel, wherein the resulting light beam output from the beam shaping optics has a flat-top shaped intensity profile along the first axis, and a Gaussian-shaped intensity profile along the second axis;
   irradiating the core stream at the interrogation zone of the flow cell with the resulting light beam output; and
   detecting light emitted from the irradiated core stream for interrogating the sample.

2. The method of claim 1, wherein the core stream flows in a direction of the second axis, and wherein a flattened top portion of the flat-top shaped intensity profile along the first axis is equal to or wider than a width of the core stream along the second axis.

3. The method of claim 1, wherein the flattened top portion of the flat-top shaped intensity profile has a coefficient of variation of less than 5%.

4. The method of claim 3, wherein the flattened top portion of the flat-top shaped intensity profile has a coefficient of variation of less than 3%.

5. The method of claim 3, wherein the flattened top portion of the flat-top shaped intensity profile has a coefficient of variation of less than 1%.

6. The method of claim 1, wherein the acylindrical lens is plano-convex and positioned to receive light on a planar side of the acylindrical lens and to output light on a convex side of the acylindrical lens, wherein the cylindrical lens is plano-convex and positioned to receive light on a convex side of the cylindrical lens and to output light on a planar side of the cylindrical lens, and wherein the acylindrical lens has an axis of symmetry orthogonal to an axis of symmetry of the cylindrical lens.

7. The method of claim 1, wherein the beam shaping optics comprises a collimating lens, the acylindrical lens is positioned between the collimating lens and the cylindrical lens.

8. The method of claim 1, comprising providing the first light beam with a light source, the light source including a fiber coupled to a laser.

9. The method of claim 1, the detecting light comprises detecting axial light loss using one or more detectors.

10. The method of claim 1, wherein the core stream comprises a sample stream positioned within a sheath fluid, wherein the sample stream is generally a single sample wide.

11. The method of claim 1, wherein the sample comprises white blood cells, red blood cells, platelets, or a hematology control.

12. A hematology instrument, comprising:
- a flow cell for streaming a hydro-dynamically focused core stream of a sample past an interrogation zone;
- beam shaping optics positioned to manipulate a first light beam, and to produce a resulting light beam that irradiates the core stream at the interrogation zone of the flow cell, wherein the beam shaping optics comprises:
- an acylindrical lens positioned to focus the first light beam in a direction of a first axis orthogonal to a direction of light travel;
- a cylindrical lens positioned to focus the light output from the acylindrical lens in a direction of a second axis orthogonal to the first axis and to the direction of light travel, wherein the cylindrical lens is positioned within a range of 15 mm to 30 mm from the acylindrical lens, wherein the resulting light beam output from the beam shaping optics has a flat-top shaped intensity profile along the first axis, and a Gaussian-shaped intensity profile along the second axis; and
- a detection system positioned to detect light emitted from the interrogation zone.

13. The hematology instrument of claim 12, wherein the core stream flows in a direction of the second axis, and wherein a flattened top portion of the flat-top shaped intensity profile along the first axis is equal to or wider than a width of the core stream along the second axis.

14. The hematology instrument of claim 12, wherein the flattened top portion of the flat-top shaped intensity profile has a coefficient of variation of less than 5%.

15. The hematology instrument of claim 12, wherein the flattened top portion of the flat-top shaped intensity profile has a coefficient of variation of less than 3%.

16. The hematology instrument of claim 12, wherein the flattened top portion of the flat-top shaped intensity profile has a coefficient of variation of less than 1%.

17. The hematology instrument of claim 12, wherein the acylindrical lens is plano-convex and positioned to receive light on a planar side of the acylindrical lens and to output light on a convex side of the acylindrical lens, wherein the cylindrical lens is plano-convex and positioned to receive light on a convex side of the cylindrical lens and to output light on a planar side of the cylindrical lens, and wherein the acylindrical lens has an axis of symmetry orthogonal to an axis of symmetry of the cylindrical lens.

18. The hematology instrument of claim 12, wherein the beam shaping optics comprises a collimating lens, the acylindrical lens positioned between the collimating lens and the cylindrical lens.

19. The hematology instrument of claim 12, comprising a light source to provide the first light beam; the light source including a fiber coupled to a laser.

20. The hematology instrument of claim 12, wherein the core stream comprises a sample stream positioned within a sheath fluid, wherein the sample stream is generally a single sample wide.

* * * * *